United States Patent [19]

Olney

[11] Patent Number: 4,945,097

[45] Date of Patent: Jul. 31, 1990

[54] ARYL-CYCLOALKYL-ALKANOLAMINES FOR TREATMENT OF NEUROTOXIC INJURY

[75] Inventor: John W. Olney, Ladue, Mo.

[73] Assignee: G. D. Searle & Co., Chicago, Ill.

[21] Appl. No.: 112,659

[22] Filed: Oct. 23, 1987

[51] Int. Cl.$^5$ .................. A61K 31/40; A61K 31/445
[52] U.S. Cl. .................................. 514/318; 514/319; 514/408
[58] Field of Search .................. 514/318, 319, 408

[56] References Cited

FOREIGN PATENT DOCUMENTS 1951614  7/1977  Fed. Rep. of Germany .

OTHER PUBLICATIONS

S. M. Rothman and J. W. Olney, *Annals of Neurology*, vol. 19, No. 2 (1986).
Anis, N. A. et al., *Br. J. Pharmacol.*, 79, 565, (1983).
J. W. Olney et al., *Neuroscience Letters*, 68, 29–34 (1986).
S. D. Berry et al., *Eur. J. Pharm.*, 96, 261–267, (1983).
M. E. Goldman et al., *FEBS Lett.*, 170, 333–336 (1985).
W. Maragos et al., *Eur. J. Pharmacol.*, 123, 173–174 (1986).
R. Quirion, *Proc. Nat'l. Acad. Sci. U.S.A.*, 78, 5881 (1981).
L. D. Snell et al., *J. Pharmacol. Exp. Ther.*, 235, 50–56 (1985).
E. H. F. Wong et al., *Proc. Nat'l. Acad. Sci. U.S.A.*, vol. 83, pp. 7104–7108 (Sep. 1986).
L. S. Goodman et al., *The Pharmacological Basis of Therapeutics*, 7th Edn., pp. 483–485, Macmillan (1975).
W. W. Fleishhaker et al., *J. Affective Disorder*, 12(2), 153–157 (1987).
E. K. G. Syvalahti et al., *Pharmacol. Toxicol. (Copenhagen)*, 60(1), 66–69 (1987).
M. Das et al., *Toxicol. Appl. Pharmacol.*, 39(1), 149–152 (1977).
N. Mann et al., *Arch. Pharm. (Weinheim, Ger.*, 309(4), 320–325, (1976).
C. Schroeder et al., *Antiviral Res.*, Suppl. 1, 95–99 (1985).
A. Hitri et al., *Psychopharmacol. Bull.*, 23 (1) 33–37 (1987).
J. P. McEvoy et al., *Psychoparmacol. Bull.*, 23(1) 30–32 (1987).

*Primary Examiner*—Stanley J. Friedman
*Attorney, Agent, or Firm*—J. Timothy Keane; Paul D. Matukaitis

[57] ABSTRACT

Compounds, compositions and methods of treatment are described to control brain damage associated with anoxia or ischemia which typically follows such conditions as stroke, cardiac arrest or perinatal asphyxia. The treatment includes administration of an aryl-cycloalkyl-alkanolamine compound as an antagonist to inhibit excitotoxic actions at major neuronal excitatory amino acid receptor sites.

9 Claims, No Drawings

ARYL-CYCLOALKYL-ALKANOLAMINES FOR TREATMENT OF NEUROTOXIC INJURY

FIELD OF THE INVENTION

This invention is in the field of clinical neurology and relates specifically to compounds, compositions and methods for neuroprotective purposes such as controlling brain damage which occurs during periods of anoxia or ischemia associated with conditions such as stroke, cardiac arrest or perinatal asphyxia.

BACKGROUND OF THE INVENTION

Unlike other tissue which can survive extended periods of hypoxia, brain tissue is particularly sensitive to deprivation of oxygen or energy. Permanent damage to neurons can occur during brief periods of hypoxia, anoxia or ischemia. Neurotoxic injury is known to be caused or accelerated by certain excitatory amino acids (EAA) found naturally in the central nervous system (CNS). Glutamate (Glu) is an endogenous amino acid which was early characterized as a fast excitatory transmitter in the mammalian brain. Glutamate is also known as a powerful neurotoxin capable of killing CNS neurons under certain pathological conditions which accompany stroke and cardiac arrest. Normally, high glutamate concentrations are maintained inside cells of the CNS by energy-dependent transport systems, but high concentrations are not allowed in the extracellular compartment where glutamate can exert excitotoxic action at excitatory synaptic receptors. Under low energy conditions such as hypoglycemia, hypoxia or ischemia, cells release glutamate and, because of the energy deficiency, the transport systems are unable to move glutamate back into the cell. Initial glutamate release stimulates further release of glutamate which results in an extracellular glutamate accumulation and a cascade of neurotoxic injury.

It has been shown that the sensitivity of central neurons to hypoxia and ischemia can be reduced by the specific antagonism of postsynaptic glutamate receptors [see S. M. Rothman and J. W. Olney, "Glutamate and the Pathophysiology of Hypoxia Ischemic Brain Damage," Annals of Neurology, Vol. 19, No. 2 (1986)]. Glutamate receptors, also known as excitatory amino acid (EAA) receptors, are of three types, each being named after the EAA glutamate analogue which selectively excites them, namely: Kainate (KA), N-methyl-D-aspartate (NMDA or NMA) and quisqualate (QUIS). Glutamate is believed to be a mixed (broad spectrum) agonist capable of binding to and exciting all three EAA receptor types.

Neurons which have EAA receptors on their dendritic or somal surfaces undergo acute excitotoxic degeneration when these receptors are excessively activated by glutamate. Thus, agents which selectively block or antagonize the action of glutamate at the EAA synaptic receptors of central neurons can prevent neurotoxic injury associated with anoxia, hypoxia or ischemia which occurs in conditions such as stroke, cardiac arrest or perinatal asphyxia.

Phencyclidine (PCP) and the PCP-like compound ketamine have been found to reduce selectively the excitatory effects of NMDA as compared to KA and QUIS [Anis, N. A. et al, "The Dissociative Anaesthetics, Ketamine and Phencyclidine, Selectively Reduce Excitation of Central Mammalian Neurones by N-Methyl-Aspartate", Br. J. Pharmacol., 79, 565 (1983)]. Blocking of NMA neurotoxicity by PCP and ketamine has been demonstrated [J. W. Olney et al., "The Anti-Excitotoxic Effects of Certain Anesthetics, Analgesics and Sedative-Hypnotics," Neuroscience Letters, 68, 29–34 (1986)].

A correlation has been found between the PCP binding effects of some PCP-derivative stereoisomers and NMDA antagonism. For example, the stereoselective effects of cis-N-(1-phenyl-4-methylcyclohexyl)piperidine and (+)-1-(1-phenylcyclohexyl)-3-methylpiperidine [(+)-PCMP] over each of their corresponding isomer counterparts in reducing the excitatory action of NMDA have been confirmed in binding and behavioral data [S. D. Berry et al, "Stereoselective Effects of Two Phencyclidine Derivatives on N-Methylaspartate Excitation of Spinal Neurones in the Cat and Rat", Eur. J. Pharm., 96, 261–267 (1983)]. Also, the compound (+)-PCMP has been found to be a potent inhibitor of the specific binding of [$^3$H]PCP to rat cerebral cortical membranes [M. E. Goldman et al, "Differentiation of $^3$H]Phencyclidine and (+)-[$^3$H]SKF-10,047 Binding Sites in Rat Cerebral Cortex", FEBS Lett., 170, 333–336 (1985)]. It has also been shown that PCP and NMA receptors are co-localized throughout much of the mammalian forebrain [W. Maragos et al, "High Correlation Between the Localization of [$^3$H]TCP Binding and NMDA Receptors", Eur. J. Pharmacol., 123, 173–174 (1986)].

Various compounds, such as arylcycloalkylamines, benzomorphans and 1,3-dioxolanes, have been identified as potential PCP receptor agonists on the basis of their ability to displace PCP receptor ligands in binding assays [R. Quirion, "Phencyclidine (Angel Dust)-/Sigma 'Opiate' Receptor: Visualization by Tritium-Sensitive Film", Proc. Nat'l. Acad. Sci. U.S.A., 78, 5881 (1981)]. These same agents have been shown to antagonize certain biological effects of NMA such as NMA-induced release of transmitter from striatal brain tissue [L. D. Snell et al, "Antagonism of N-Methyl-D-Aspartate-Induced Transmitter Release In The Rat Striatum By Phencyclidine-Like Drugs And Its Relationship To Turning Behavior", J. Pharmacol. Exp. Ther., 235, 50–56, (1985)].

The compound MK-801 {(+)-5-methyl-10,11-dihydro-5H-dibenzo[a,d]cyclohepten-5,10-imine maleate)} has been found to be a potent, selective non-competitive antagonist of the N-methyl-D-aspartate receptor site [E. H. F. Wong et al, "The Anticonvulsant MK-801 Is A Potent N-Methyl-D-Aspartate Antagonist", Proc. Nat'l. Acad. Sci U.S.A., Vol. 83, pp. 7104–7108 (Sept. (1986)].

Well-known competitive NMA antagonists, such as D-α-amino-5-phosphonopentanoate, are capable of effectively blocking the excitotoxic effects of NMA. But such compounds show little therapeutic promise in treatment or prevention of ischemic brain damage because these compounds do not penetrate the blood-brain barrier.

Compounds such as procyclidine, biperiden and trihexyphenidyl are known to have anti-cholinergic actions and have been identified for treatment of Parkinsonism. Such compounds are known to ameliorate the muscle rigidity and akinesia associated with Parkinsonism and extrapyramidal symptoms associated with neuroleptic drug treatment [L. S. Goodman et al, The Pharmacological Basis of Therapeutics, 5th Edn., Macmillan (1975)].

Aryl-cycloalkyl-alkanolamine compounds and derivatives have been described for various pharmaceutical purposes. For example, the compound α-bicyclo[2.2.1-]hept-5-en-2-yl-α-phenyl-1-piperidinepropanol, commonly known as biperiden, has been studied for its mood altering effects [W. W. Fleischhacker et al, J. Affective Disorder, 12 (2), 153-157 (1987)], and for its interaction with brain muscarinic cholinoceptors [E. K. G. Syvalahti et al, Pharmacol. Toxicol. (Copenhagen), 60 (1), 66-69 (1987)]. The hydrochloride salt of biperiden has been studied for its interaction with nicotine and oxotremorine in rat diaphragm [M. Das et al, Toxicol. Appl. Pharmacol., 39 (1), 149-152 (1977). U.S. Pat. No. 2,891,890 describes the compound α-cyclohexyl-α-phenyl-1-pyrrolidinepropanol hydrochloride and its free base, commonly known as procyclidine, which is an anti-cholinergic compound having anti-convulsant properties. U.S. Pat. No. 4,031,245 mentions the compound α-cyclopropyl-α-[3-(trifluoromethyl)phenyl]-1-piperidinepropanol and its hydrochloride derivative in a description of alkenyl and alkanylamines for treating depression. U.S. Pat. No. 3,553,225 mentions the compound α-phenyl-α-tricyclo[3,3,1,13,7]dec-1-yl-1-piperidinebutanol in a description of adamantane derivatives as tranquilizers. West German Offen. No. 1,951,614, in a description of benzyl alcohol derivatives having sedative and ulcer-preventing properties, mentions the compounds a-(4-amino-3,5-dibromophenyl)-a-cyclohexyl-1-piperidinebutanol, α-(4-amino-3-chlorophenyl)-α-cyclohexylhexahydro-1H-azepine-1-butanol, α-(4-amino-3,5-dichlorophenyl)-α-cyclohexylhexahydro-1H-azepine-1-butanol and α-(4-amino-3,5-dibromophenyl)-α-cyclohexyl-1,8,8-trimethyl-3-azabicyclo[3,2,-1]octane-3-butanol. The compound α-[1,1'-biphenyl]-4-yl-o-cyclohexyl-1piperidinepropanol hydrochloride was mentioned in a study of the potential analgetic activity of some reduced biphenyl Mannich bases [N. Mann et al, Arch. Pharm. (Weinheim, Ger.), 309 (4), 320-325 (1976)]. The compound α-phenyl-α-tricyclo[2.2.1.02,6hept-3-yl-1-piperidinepropanol hydrochloride, commonly known as triperiden, is a known anti-Parkinsonism agent also having anti-viral properties [C. Schroeder et al, Antiviral Res., Suppl. 1, 95-99 (1985)]. The compound α-cyclohexyl-α-phenyl-1-piperidinepropanol, commonly known as trihexyphenidy], is a known anti-Parkinsonian which has been studied for its effects in schizophrenic patients [A. Hitri et al, Psychopharmacol. Bull., 23 (1) 33-37 (1987) and for its effects on memory in elderly patients [J. P. McEvoy et al, Psychopharmacol. Bull., 23 (1), 30-32 (1987)].

DESCRIPTION OF THE INVENTION

Control of exoitotoxic neuropathological processes and the neurodegenerative consequences thereof in mammals is provided by treating a susceptible mammal with an anti-excitotoxic effective amount of a compound of a class of aryl-cycloalkyl-alkanolamines represented by Formula I:

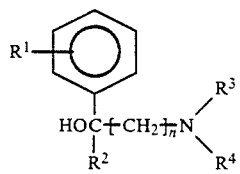

(I)

wherein $R^1$ is one or more groups independently selected from hydrido, halo, alkyl, acyl, hydroxyalkyl, haloalkyl, aminoalkyl, alkoxy, amino, alkylamino and acylamino; wherein $R^2$ is selected from hydrido, cycloalkyl, cycloalkenyl, halocycloalkyl, alkylcycloalkyl, acylcycloalkyl, hydroxycycloalkyl, haloalkylcycloalkyl, aminoalkylcycloalkyl, alkoxycycloalkyl, aminocycloalkyl, bicycloalkyl, bicycloalkenyl and tricycloalkyl wherein the bicycloalkyl, bicycloalkenyl and tricycloalkyl groups may be substituted with one or more groups selected from alkyl, halo, acyl, hydroxy, hydroxyalkyl, haloalkyl, acyl, alkoxy, amino and alkylamino; wherein each of $R^3$ and $R^4$ is independently selected from hydrido, alkyl, acyl, alkenyl, cycloalkyl, phenylalkyl, phenyl, aminoalkyl and alkylaminoalkyl; and wherein $R^3$ and $R^4$ may be taken together to form a cyclic group including the nitrogen atom of Formula I, and n is an integer selected from one through five.

A preferred class of compounds within Formula I consists of those compounds wherein $R^1$ is one or more groups independently selected from hydrido, halo, alkyl, haloalkyl, aminoalkyl, alkoxy, amino and acylamino; wherein $R^2$ is selected from cycloalkyl, cycloalkenyl, alkylcycloalkyl, bicycloalkyl, bicycloalkenyl, tricycloalkyl, alkylbicycloalkyl, alkylbicycloalkenyl and tricycloalkyl; and wherein each of $R^3$ and $R^4$ is independently selected from alkyl, acyl, alkenyl, cycloalkyl of three to about ten carbon atoms, benzyl, phenyl and alkylaminoalkyl, and wherein $R^3$ and $R^4$ may be taken together to form a cyclic group containing from three to ten ring atoms including the nitrogen atom of Formula I; wherein n is an integer selected from two through five.

A more preferred class of compounds within Formula I consists of those compounds wherein $R^1$ is one or more groups independently selected from hydrido, fluoro, chloro, bromo, lower alkyl, fluoroalkyl, chloroalkyl, alkoxy, amino and acylamino wherein $R^2$ is selected from cycloalkyl and cycloalkenyl each of three to ten carbon atoms, and bicycloalkyl and bicycloalkenyl of seven to twelve carbon atoms of which cycloalkyl, cycloalkenyl, bicycloalkyl, bicycloalkenyl and tricycloalkyl groups may be substitutable positions by lower alkyl; and wherein $R^3$ and $R^4$ form a cyclic group of three to ten ring atoms including the nitrogen atom of Formula I; wherein n is an integer selected from two through four.

An even more preferred class of compounds within Formula I consists of those compounds wherein $R^1$ is one or more groups selected from hydrido, fluoro, chloro, bromo, methyl, ethyl, n-propyl, isopropyl, n-butyl, iso-butyl, sec-butyl, tert-butyl, trifluoromethyl, 2,2,2-trifluoromethyl, perfluoroethyl, methoxy, ethoxy, n-propoxy, iso-propoxy, n-butoxy, iso-butoxy, 2,2-dimethylpentoxy, n-pentoxy, amino and aminoacyl; wherein $R^2$ is selected from cyclopropyl, cyclobutyl, cyclopentyl, cyclohexyl, cyclohexenyl, cycloheptyl, methylcyclopropyl and bicycloheptenyl; and wherein $R^2$ and $R^4$ form a saturated N-containing cyclic group having two to seven carbon atoms which N-containing cyclic group contains a single nitrogen atom of Formula I.

A most preferred class of compounds of Formula I consists of those compounds wherein $R^1$ is hydrido; $R^2$ is selected from cyclopentyl, cyclohexyl, cyclohexenyl and bicycloheptenyl; $R^2$ and $R^4$ form an N-containing cyclic group including the nitrogen atom of Formula I and including four to six ring carbon atoms; and wherein n is two.

Within this most preferred class of compounds of Formula I is the following class of particularly preferred compounds:

α-cyclohexyl-α-phenyl-1-pyrrolidinepropanol hydrochloride (common name "procyclodine hydrochloride");
α-cyclohexyl-αenyl-1-piperidinepropanol (common name "trihexyphenidyl");
α-cyclohexyl-α-phenyl-1-piperidinepropanol hydrochloride (common name "trihexyphenidyl hydrochloride");
α-bicyclo2.2.1]hept-5-en-2-yl-α-phenyl-1-piperidinepropanol (common name "biperiden");
α-bicyclo[2.2.1]hept-5-en-2-yl-α-phenyl-1-piperidinepropanol hydrochloride (common name "biperiden hydrochloride"):
3,3,5-trimethyl-α-phenyl-α-2-(1-piperidinyl)ethylcyclohexanemethanol;
4-hydroxy-α-4-diphenyl-α-tricyclo[2.2.1.02,6]hept-1-yl-1-piperidinepropanol;
α-cyclopropyl-α-[3-(trifluoromethyl)phenyl]-1piperidinepropanol hydrochloride;
α-phenyl-α-tricyclo[3.3.1.13,7]dec-1-yl-1-piperidinebutanol;
α-phenyl-α-tricyclo[2.2.1.02,6]hept-3-yl -1-piperidinepropanol hydrochloride;
α-(4-amina-3,5-dibromophenyl)-α-cyclohexyl-1-piperidinebutanol;
α-(p-chorophenyl)-α-cyclohexyl-1-piperidinepropanol hydrochloride
α-(4-amina-3-chlorophenyl)-α-cyclohexylhexahydro-1H-azepine-1-butanol;
α-cyclohexyl-α-(p-methoxyphenyl)-1-piperidinepropanol;
α-(4-amino-3,5-dichlorophenyl)-α-cyclohexylhexahydro-1H-azepine-1-butanol;
α-(4-amino-3,5-dibromophenyl)-α-cyclohexyl-1,8,8-trimethyl-3-azabicyclo[3.2.1]octane-3-butanol;
α-[1,1'-biphenyl]-4-yl-a-cyclohexyl-1-piperidinepropanol hydrochloride;
α-phenyl-α-tricyclo3.3.1.13,7]dec-1-yl-1-pyrrolidinepropanol hydrochloride;
α-phenyl-α-tricyclo[2.2.1.02,6]hept-3-yl-1-piperidinepropanol hydrochloride (common name "triperidene hydrochloride");
α-(3,3-dimethylbicyclo[2.2.1]hept-2-yl)-α-phenyl-1-piperidinepropanol;
α-cyclohexyl-4-hydroxy-α-4-diphenyl-1-piperidinepropanol;
α-cyclopropyl-α-[3-(trifluoromethyl)phenyl]-1-piperidinepropanol;
α-cyclohexyl-α-phenyl-3-azabicyclo[3.2.2]nonane-3-propanol hydrochloride.

Of highest interest of the particularly preferred compounds are procyclidine, trihexyphenidyl, biperiden and their hydrochloride salts, Other specific compounds of interest within Formula I are as follows:
α-[2-(diethylamino)ethyl]-α-phenylcyclohexanemethanol;
α-cyclopentyl-α-(3-(dimethylaminopropyl]-p-methoxybenzyl alcohol;
α-[3-(dimethylamino)propyl]-α-(α,α,α-trifluoro-m-tolyl)cyclohexanemethanol;
α-[3-(dimethylamino)propyl]-α-m-tolylcyclohexanemethanol;
α-(p-bromophenyl)-α-[3-(dimethylamino)propyl]cyclohexanemethanol;
α-(p-chlorophenyl)-α-[3-(dimethylamino)propyl]cyclohexanemethanol;
m-chloro-α-cyclopentyl-α-[3-(dimethylamino)propyl]-benzyl alcohol;
α-cyclopentyl-α-[3-(dimethylamino)propyl]benzyl alcohol;
α-[2-(dimethylamino)ethyl]-α-(p-methoxyphenyl)cyclohexanemethanol hydrochloride;
α-[2-(diethylamino)ethyl]-α-(p-methoxyphenyl)cyclohexanemethanol;
α-(p-chlorophenyl)-α-2-(dimethylamino)ethyl]cyclohexanemethanol;
α-(p-chlorophenyl)-α-2-(dimethylamino)ethyl]cyclohexanemethanol hydrochloride;
α-(p-chlorophenyl)-α-[2-(diethylamino)ethyl]cyclohexanemethanol;
α-(p-chlorophenyl)-α-[2-(diethylamino)ethyl]cyclohexanemethanol hydrochloride;
α-(p-bromophenyl)-α-[2-(diethylamino)ethyl]cyclohexanemethanol hydrochloride;
α-(p-bromophenyl)-α-[2-(diethylamino)ethyl]cyclohexanemethanol hydrochloride;
α-[2-(diethylamino)ethyl]-α-phenylcyclohexanemethanol hydrochloride;
α-(3-dimethylaminopropyl)-α-phenylcyclohexanemethanol hydrochloride;
α-(2-dimethylaminoethyl)-α-phenyl-1-cyclohexene-1-methanol;
α-[5-[(2-diethylaminoethyl)methylamino]pentyl]-α-phenylcyclohexanemethano;
α-[2-(dimethylamino)ethyl]-α-(p-propoxyphenyl)cyclohexanemethanol;
α-[2-(dimethylamino)ethyl]-α-(p-propoxyphenyl)cyclohexanemethanol hydrochloride;
α-[2-(dimethylamino)ethyl]-α-(p-methoxyphenyl)cyclohexanemethanol;
α-[2-(dimethylamino)ethyl]-α-(p-ethoxyphenyl)cyclohexanemethanol;
α-[2-(dimethylamino)ethyl]-α-(p-ethoxyphenyl)cyclohexanemethanol hydrochloride;
α-[2-(dimethylamino)ethyl]-α-(p-isopropoxyphenyl)cyclohexanemethanol;
α-[2-(dimethylamino)ethyl]-α-(p-isopropoxyphenyl)cyclohexanemethanol hydrochloride;
α-(p-butoxyphenyl)-α-[2-(dimethylamino)ethyl]cyclohexanemethanol;
α-[2-(dimethylamino)ethyl]-α-(p-isobutoxyphenyl)cyclohexanemethanol;
α-[2-(dimethylamino)ethyl]-α-(p-isobutoxyphenyl)-cyclohexanemethanol hydrochloride;
α-[2-(dimethylamino)ethyl]-α-(p-isopentyloxy)phenylcyclohexanemethanol;
α-[2-(dimethylamino)ethyl]-α-(p-isopentyloxy)phenylcyclohexanemethanol hydrochloride;
α-[2-(dimethylamino)ethyl-α-phenylcyclohexanemethanol;
α-[2-(dimethylamino)ethyl]-α-phenylcyclohexanemethanol hydrochloride;
α-2-(dimethylamino)ethyl]-α-(p-pentyloxy)phenyl]cyclohexanemethanol;
α-(4-amino-3-bromophenyl)-α-[3-diethylamino)propyl]cyclohexanemethanol;
α-(4-amino-3-chlorophenyl)-α-[3-diethylamino)propyl]cyclohexanemethanol;
α-(4-amino-3,5-dichlorophenyl)-α-[3-dimethylamino)propyl]cyclohexanemethanol;

α-(4-amino-3,5-dichlorophenyl)-α-[3-diethylamino)-propyl]cyclohexanemethanol;
α-(4-amino-3,5-dibromophenyl)-α-[3-dimethylamino)-propyl]cyclohexanemethanol;
α-(4-amino-3,5-dibromophenyl)-α-[3-(ethylmethylamino)propyl]cyclohexanemethanol;
α-(4-amino-3,5-dibromophenyl)-α-[3-(diethylamino)-propyl]cyclohexanemethanol;
α-(4-amino-3,5-dibromophenyl)-α-[3-(dipropylamino)-propyl]cyclohexanemethanol;
α-(4-amino-3,5-dibromophenyl)-α-[3-(diallylamino)-propyl]cyclohexanemethanol;
α-(4-amino-3,5-dibromophenyl)-α-[3-(dibutylamino)-propyl]cyclohexanemethanol;
α-(4-amino-3,5-dibromophenyl)-α-[3-(cyclohexylmethylamino)propyl]cyclohexanemethanol;
α-(4-amino-3,5-dibromophenyl)-α-[3-(benzylmethylamino)propyl]cyclohexanemethanol;
α-(4-amino-3,5-dibromophenyl)-α-[3-(N-methylanilino)propyl]cyclohexanemethanol;
N-[2,6-dichloro-4-1-cyclohexyl-[4-(diethylamino)-1-hydroxybutyl]phenyl]acetamide;
α-cyclopropyl-α-[2-(dimethylamino)ethyl]benzenemethanol hydrochloride;
α-cyclopropyl-α-[3-(dimethylamino)propyl]benzenemethanol;
α-cyclopropyl-α-[2-(dimethylamino)ethyl]-4-methoxybenzenemethanol hydrobromide;
α-cyclopropyl-α-[2-(dimethylamino)ethyl]-3-(trifluoromethyl)benzenemethanol hydrochloride;
α-cyclopropyl-α-[2-(dimethylamino)ethyl]benzenemethanol;
α-cyclopropyl-α-[3-(dimethylamino)propyl]benzenemethanol hydrochloride;
α-cyclopropyl-α-[2-(dimethylamino)ethyl]-4-methoxybenzenemethanol;
α-cyclopropyl-α-[2-(dimethylamino)ethyl]-3-(trifluoromethyl)benzenemethanol;
N-[3-cyclopropyl-3-hydroxy-3-[3-(trifluoromethyl)-phenyl]propyl]-N-methylacetamide;
3-chloro-α-cyclopropyl-α-[2-(dimethylamino)ethyl]-benzenemethanol hydrochloride;
α-cyclopropyl-α-[2-(dimethylamino)ethyl]-4-(trifluoromethyl)benzenemethanol hydrochloride;
α-cyclopropyl-α-[2-(diethylamino)ethyl]-3-(trifluoromethyl)benzenemethanol hydrochloride;
α-[(dimethylamino)methyl]-α-(2-methylcyclopropyl)-benzenemethanol;
α-cyclopropyl-α-[2-(dimethylamino)ethyl]-4-(trifluoromethyl)benzenemethanol;
α-cyclopropyl-α-[2-(diethylamino)ethyl]-3-(trifluoromethyl)benzenemethanol;
3-chloro-α-cyclopropyl-α-[2-(dimethylamino)ethyl]-benzenemethanol;
α-(2-diethylaminoethyl)-α-phenyl-5-norbornene-2-methanol;
α-(2-diethylaminoethyl)-α-phenyl-1-cyolohexene-1-methanol;
α-(3-dimethylaminopropyl)-α-phenyl-cyclohexanemethanol.

The term "hydrido" denotes a single hydrogen atom (H) which may be attached, for example, to a carbon atom or to an oxygen atom to form an hydroxyl group. Where the term "alkyl" is used, either alone or within other terms such as "haloalkyl" and "hydroxyalkyl", the term "alkyl" embraces linear or branched radicals having one to about ten carbon atoms. Preferred alkyl radicals are "lower alky" radicals having one to about five carbon atoms. The term "cycloalkyl" embraces radicals having three to about ten carbon atoms, such as cyclopropyl and cyclobuty. The term "haloalkyl" embraces radicals wherein any one or more of the alkyl carbon atoms is substituted with one or more halo groups, preferably selected from bromo, chloro and fluoro. Specifically embraced by the term "haloalkyl" are monohaloalkyl, dihaloalkyl and polyhaloalkyl groups. A monohaloalkyl group, for example, may have either a bromo, a chloro, or a fluoro atom within the group. Dihaloalky and polyhaloalkyl groups may be substituted with two or more of the same halo groups, or may have a combination of different halo groups. A dihaloalkyl group, for example, may have two bromo atoms, such as a dibromomethyl group, or two chloro atoms, such as a dichloromethyl group, or one bromo atom and one chloro atom, such as a bromo-chloromethyl group. Examples of a polyhaloalkyl are trifluoromethyl, 2,2,2-trifluoroethyl, perfluoroethyl and 2,2,3,3-tetrafluoropropyl groups. The terms "alkylol" and "hydroxylalkyl" embrace linear or branched alkyl groups having one to ten carbon atoms any one of which may be substituted with one or more hydroxyl groups. The terms "alkenyl" embraces linear or branched radicals having two to about ten carbon atoms and containing at least one carbon-carbon double bond. The terms "alkoxy" and "alkoxyalkyl" embrace linear or branched oxy-containing radicals having alkyl portions of one to ten carbon atoms, such as methoxy group. The "alkoxy" or "alkoxyalkyl" radicals may be further substituted with one or more halo atoms, such as fluoro, chloro or bromo, to provide haloalkoxy or haloalkoxyalkyl groups. Examples of other substituents forming compounds of Formula I are as follows:

| Substituent Name | Structure |
| --- | --- |
| alkylcycloalkyl | (cyclopropyl with CH₃) |
| acylcycloalkyl | (cyclopentyl with —C(=O)CH₃) |
| halocycloalkyl | (cyclohexyl with two Cl) |
| hydroxycycloalkyl | (cyclopentyl with —OH) |
| haloalkylcycloalkyl | (cyclohexyl with —CF₃) |
| aminoalkylcycloalkyl | (cycloheptyl with —NH₂) |

-continued

| Substituent Name | Structure |
|---|---|
| bicycloalkyl | (bicycloalkyl structure) |
| bicycloalkenyl | (bicycloalkenyl structure) |
| tricycloalkyl | (tricycloalkyl structure) |

Specific examples of alkyl groups are methyl, ethyl, n-propyl, isopropyl, n-butyl, sec-butyl, iso-butyl, tert-butyl, n-pentyl, iso-pentyl, methylbutyl, dimethylbutyl and neopentyl. Typical alkenyl and alkynyl groups may have one unsaturated bond, such as an allyl group, or may have a plurality of unsaturated bonds, with such plurality of bonds either adjacent, such as allene-type structures, or in conjugation, or separated by several saturated carbons.

Included within the family of compounds of Formula I, are the tautomeric forms of the described compounds, isomeric forms including diastereomers, and the pharmaceutically-acceptable salts thereof. The term "pharmaceutically-acceptable salts" embraces salts commonly used to form alkali metal salts and to form addition salts of free acids or free bases. Since the compounds of Formula I contain basio nitrogen atoms, such salts are typically acid addition salts. The nature of the salt is not critical, provided that it is pharmaceutically acceptable, and acids which may be employed to form such salts are, of course, well known to those skilled in this art. Examples of acids which may be employed to form pharmaceutically acceptable acid addition salts include such inorganic acids as hydrochloric acid, sulphuric acid and phosphoric acid and such organic acids as maleic acid, succinic acid and citric acid. Other salts include salts with alkali metals or alkaline earth metals, such as sodium, potassium, calcium and magnesium. All of these salts may be prepared by conventional means from the corresponding compound of Formula I by reacting, for example, the appropriate acid with the compound of Formula I.

Methods of synthesis of representative compounds of Formula I are known. For example, synthesis of procyclidine and its salts are shown in U.S. Pat. Nos. 2,891,890 and 2,826,590. Synthesis of trihexyphenidyl hydrochloride is described in U.S. Pat. No. 2,682,543. Synthesis of biperiden is described in U.S. Pat. No. 2,789,110.

BIOLOGICAL EVALUATION

Prevention of the neurodegenerative consequences associated with conditions of hypoxia or ischemia may be accomplished with administration of a compound of Formula I. In particular, the compounds procyclidine, biperiden and trihexyphenidyl were evaluated in biological assays designed to detect compounds capable of inhibiting hypoxia- or ischemia-induced neuronal degeneration.

NMDA/KA Antagonist Assay

A 15-day old chick embryo retina, incubated for 30 min. in a balanced sat solution (BSS) containing 1 mM Glu, developed a full lesion resembling that described in the immature mouse retina following s.c. administration of Glu. Other excitotoxin agonists also produce acute lesions within 30 min., each agent being effective at a concentration proportional to its known excitatory and toxic potencies. The pattern of cellular degeneration is restricted in each case to the ganglion cell, inner plexiform and inner nuclear layers, but within these areas certain agonists induce different patterns of degeneration, the differences being most pronounced between NMA and KA. Two agonists were employed in the present test, each at a concentration established previously to be the lowest concentration required to consistently cause a fully-developed retinal lesion: KA (25 $\mu$M) and NMA (200 $\mu$M). Procyclidine, biperiden and trihexyphenidyl were tested at various concentrations for their ability to prevent KA or NMA neurotoxicity. Although partial blocking was observed for antagonist concentrations below the threshold for complete protection, the criterion used for comparing agents for antagonist potency was the concentration required to completely prevent KA or NMA from exerting any toxic activity in any specimen (n>6) studied at that concentration. Internal controls in each experiment consisted of at least six specimens being incubated with agonist alone. A typical toxic reaction had to be present in all controls and absent from all experimental specimens in order to qualify as a blocking effect. The method of tissue preparation was as follows: 15-day old chick embryos were decapitated and their eyes removed and cut into quadrants after excising the cornea and removing the lens, vitreous and iris. The retinal quadrants were then gently separated from the pigment epithelium and incubated for 30 min. at 37° C. in BSS to which an agonist or agonist plus antagonist was added. The BSS contained 140 mM Na+, 5.0 mM K+, 0.5 mM Ca++, 4 5 mM mG++, 150 mM Cl−, 5.6 mM glucose and bicarbonate/phosphate buffer (pH 7.3). After incubation for 30 min., the retinal quadrants were fixed by immersion in phosphate-buffered solution containing 1.5% glutaraldehyde and 1% paraformaldehyde, then additionally fixed in 1% osmium tetroxide, dehydrated in graded ethanols, cleared in toluene and embedded in araldite. Sections were cut 1 micron thick on a Sorval ultratome and stained with Methylene blue/Azure 11 for histopathological evaluation by light microscopy. Data are summarized in Table I in which the antagonist potency is given as the concentration ($\mu$M) required to totally prevent a neurotoxic reaction. A dash signifies no antagonist action.

TABLE I

| Antagonist Tested | vs NMA | vs KA |
|---|---|---|
| Procyclidine | 15 $\mu$M | — |
| Trihexyphenidyl | 125 $\mu$M | — |
| Biperiden | 200 $\mu$M | — |

Receptor Binding Assay

For receptor binding, frozen brain sections (10 microns) were incubated in 5 $\mu$M tris acetate (pH 7.25) containing 0.5 mM magnesium acetate and 20 nM $^3$H-TCP for 45 min. at 4° C. Non-specific binding was assessed with 200 $\mu$M PCP. Inhibition of $^3$H-TCP binding was studied by including potential inhibitors in the sH-TCP incubation at concentrations from 10 nM to 1 mM. Dissociation and inhibition constants were calculated by Scatchard/Rosenthal analysis of data obtained by liquid scintillation counting of whole sections. Procylidine effectively inhibited binding of sH-TCP with a $K_i$ value of 5.76.

In Vivo Hypoxia/Ischemia (H/I) Assay

A total of 30 Sprague Dawley rats, 10 days old, were used in this assay. Ten pups (5 control and 5 experimental) were studied on each of 3 separate days, the protocol being the same each day. A unilateral carotid ligation was performed under halothane anesthesia, and the incision was closed with super glue. After recovery from anesthesia, the experimental pups were given a subcutaneous injection of procyclidine (50 mg/kg in 0.1 ml aqueous solution, pH 7.4) and controls an equal volume sc injection of normal saline. Immediately thereafter, all 10 of the pups (half control and half experimental) were placed together in a large sealed transparent chamber and a partial vacuum was gradually created (pressure reduced from 760 to 200 mm Hg over a 1 minute period). A water bath surrounding the bottom half of the chamber kept the temperature inside at 38° C. After 75 minutes the pressure was returned gradually to 760 mm Hg over a 1 minute interval and, after a 2 hour observation period, the pups were anesthetized, the neck incision opened and the ligature removed from the carotid (a piece of tubing had originally been placed between the suture and vessel wall to facilitate subsequent removal of the suture without damage to the vessel wall). While still under anesthesia, the pups were sacrificed by perfusion fixation with aldehyde fixatives. Since the ligature had been removed from the occluded carotid, perfusate was able to distribute equally to the two hemispheres. After 15 minutes of perfusion, the brains were removed and sliced in 1 mm thick transverse slabs which were post fixed in osmium tetroxide, dehydrated in graded ethanols, cleared in toluene and embedded flat in araldite [J. W. Olney, "Glutamate-Induced Neuronal Necrosis In The Infant Mouse Hypothalamus: An Electron Microscopic Study", *Neuropthol. Exp. Neurol.*, 30, 75–90 (1971)]. Sections (1 micron thick) were cut at 40 micron intervals and stained with azure II/methylene blue to permit a systematic microscopic evaluation of all regions of interest in each brain. In a large number of control infant rats (n>100) subjected to the above hypobaric-/ischemic conditions, there has been shown a 90% survival rate (10% die in the hypobaric chamber) and a 94% incidence of brain damage which is always confined unilaterally to the side of the carotid ligation [J. M. Olney, "Hypoxia-Ischemia Causes Glutamate-Like Neuropathological changes in Infant Rat Brain", *Neurosci Abst.*, 13, 1553 (1987)]. Also, unilateral carotid ligation by itself or the above hypobaric procedure by itself does not result in brain damage in 10 day old rats. The damage in control rats consists of unilateral disseminated acute neuronal degeneration in some or all of the following regions: medial habenulum, dentate hippocampal gyrus, caudate nucleus, olfactory tubercle, islands of calleja, fronto-parietal neocortex and several thalamic nuclei. Two of 15 control and 2 of 15 experimental infants died in the hypobaric chamber. Among the remaining control infants, each subjected to the same conditions as experimentals except that they did not receive procyclidine, all 13 had disseminated lesions as above described. Among the 13 surviving procyclidine-treated pups, 10 had no damage in any of the above brain regions, 3 had small attenuated lesions, limited in two pups to the medial habenulum and in one to the caudate. Thus, procyclidine provided total protection against H/I neuronal degeneration in almost 80% of treated animals and markedly reduced the severity of neuropathology in the remaining 20%. The single dose employed (50 mg/kg) produced minimal side effects. Signs such as ataxia, head and body weaving, prostration and respiratory depression, which are sometimes seen in animals treated with antiexcitotoxic drugs, were not observed. The mortality rate in experimentals was the same as in the concurrent controls (and historical controls).

Administration of compounds within Formula I to humans can be by any technique capable of introducing the compounds into the bloodstream of a human patient, including oral administration, and by intravenous, intramuscular and subcutaneous injections.

Compounds indicated for prophylactic therapy will preferably be administered in a daily dose generally in a range from about 0.1 mg to about 10 mg per kilogram of body weight per day. A more preferred dosage will be a range from about 0.2 mg to about 5 mg per kilogram of body weight. Most preferred is a dosage in a range from about 0.3 to about 2.5 mg per kilogram of body weight per day. A suitable dose can be administered, in multiple sub-doses per day. These sub-doses may be administered in unit dosage forms. Typically, a dose or sub-dose may contain from about 1 mg to about 100 mg of active compound per unit dosage form. A more preferred dosage will contain from about 2 mg to about 50 mg of active compound per unit dosage form. Most preferred is a dosage form containing from about 3 mg to about 25 mg of active compound per unit dose.

The active compound is usually administered in a pharmaceutically-acceptable formulation, although in some acute-care situations a compound of Formula I may be administered alone. Such formulations may comprise the active compound together with one or more pharmaceutically-acceptable carriers or diluents. Other therapeutic agents may also be present in the diluent provides an appropriate vehicle for delivery of the active compound without introducing undesirable side effects. Delivery of the active compound in such formulations may be by various routes including oral, nasal, topical, buccal and sublingual, or by parenteral administration such as subcutaneous, intramuscular, intravenous and intradermal routes.

Formulations for oral administration may be in the form of capsules containing the active compound dispersed in a binder such as gelatin or hydroxypropylmethyl cellulose, together with one or more of a lubricant, preservative, surface-active or dispersing agent. Such capsules or tablets may contain controlled-release formulation as may be provided in a disposition of active compound in hydroxypropylmethyl cellulose.

Formulations for parenteral administration may be in the form of aqueous or non-aqueous isotonic sterile injection solutions or suspensions. These solutions and suspensions may be prepared from sterile powders or granules having one or more of the carriers or diluents mentioned for use in the formulations for oral administration.

Although this invention has been described with respect to specific embodiments, the details of these embodiments are not to be construed as limitations.

Various equivalents, changes and modifications may be made without departing from the spirit and scope of this invention, and it is understood that such equivalent embodiments are part of this invention.

What is claimed is:

1. A method to control excitotoxic neuropathological processes and the neurodegenerative consequences thereof in mammals, which method comprises treating a mammal susceptible to or suffering from anoxia, hypoxia or ischemia with a therapeutically-effective amount of a compound of the formula

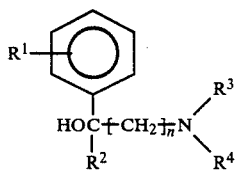

wherein $R^1$ is one or more groups independently selected from hydrido, halo, alkyl, acyl, hydroxyalkyl, haloalkyl, aminoalkyl, alkoxy, amino alkylamino and acylamino; wherein $R^2$ is selected from hydrido, cycloalkyl, cycloalkenyl, halocycloalkyl, alkylcycloalkyl, acylcycloalkyl, hydroxycycloalkyl, haloalkylcycloalkyl, aminoalkylcycloalkyl, alkoxycycloalkyl, aminocycloalkyl, bicycloalkyl, bicycloalkenyl and tricycloalkyl wherein the bicycloalkyl, bicycloalkenyl and tricycloalkenyl groups may be substituted with one or more groups selected from alkyl, halo acyl, hydroxy, hydroxyalkyl, haloalkyl, acyl, alkoxy, amino and alkylamino; wherein each of $R^3$ and $R^4$ is independently selected from hydrido, alkyl, acyl, alkenyl, cycloalkyl, phenylalkyl, phenyl, aminoalkyl and alkylaminoalkyl; and wherein $R^3$ and $R^4$ together to form a cyclic group including the nitrogen atom of Formula I, and n is an integer selected from one through five.

2. The method of claim 1 wherein $R^1$ is one or more groups independently selected from hydrido, halo, alkyl, haloalkyl, aminoalkyl, alkoxy, amino and acylamino; wherein $R^2$ is selected from cycloalkyl, cycloalkenyl, alkylcycloalkyl, bicycloalkyl, bicycloalkenyl, tricycloalkyl, alkylbicycloalkyl, alkylbicycloalkenyl and tricycloalkyl; and wherein $R^3$ and $R^4$ together to form a cyclic group containing from three to ten ring atoms including the nitrogen atom of Formula I; wherein n is an integer selected from two through five.

3. The method of claim 2 wherein $R^1$ is one or more groups independently selected from hydrido, fluoro, chloro, bromo, lower alkyl, fluoroalkyl, chloroalkyl, alkoxy, amino and acylamino; wherein $R^2$ is selected from cycloalkyl and cycloalkenyl each of three to ten carbon atoms; and bicycloalkyl and bicycloalkenyl of seven to twelve carbon atoms of which cycloalkyl, cycloalkenyl and bicycloalkyl, bicycloalkenyl and tricycloalkyl groups may be substitutable positions by lower alkyl; and wherein $R^3$ and $R^4$ form a cyclic group of three to ten ring atoms including the nitrogen atom of Formula I; wherein n is an integer selected from two through four.

4. The method of claim 3 wherein $R^1$ is one or more groups selected from hydrido, fluoro, chloro, bromo, methyl, ethyl, n-propyl, isopropyl, n-butyl, iso-butyl, sec-butyl, tert-butyl, trifluoromethyl, 2,2,2-trifluoromethyl, perfluoroethyl, methoxy, ethoxy, n-propoxy, iso-propoxy, n-butoxy, iso-butyl, 2,2-dimethylpentoxy, n-pentoxy, amino and aminoacyl; wherein $R^2$ is selected from cyclopropyl, cyclobutyl, cyclopentyl, cyclohexyl, cyclohexenyl, cycloheptyl, methylcyclopropyl and bicycloheptenyl; and wherein $R^3$ and $R^4$ form a saturated N-containing cyclic group having two to seven carbon atoms which N containing cyclic group contains a single nitrogen atom of Formula I.

5. The method of claim 4 wherein $R^1$ is hydrido; $R^2$ is selected from cyclopentyl, cyclohexyl, cyclohexenyl and bicycloheptenyl; $R^3$ and $R^4$ form an N-containing cyclic group including the nitrogen atom of Formula I and including four to six ring carbon atoms; and wherein n is two.

6. The method of claim 1 wherein said compound is selected from

α-cyclohexyl-α-phenyl-1-pyrrolidinepropanol hydrochloride;
α-cyclohexyl-α-phenyl-1-piperidinepropanol;
α-cyclohexyl-α-phenyl-1-piperidinepropanol hydrochloride;
α-bicyclo[2.2.1]hept-5-en-2-yl-α-phenyl-1-piperidinepropanol;
α-bicyclo[2.2.1]hept-5-en-2-yl-α-phenyl-1-piperidinepropanol hydrochloride;
3,3,5-trimethyl-α-phenyl-α-[2-(1-piperidinyl)ethylcyclohexanemethanol;
4-hydroxy-α-4-diphenyl-α-tricyclo[2.2.1.02,6]hept-1-yl-1-piperidinepropanol
α-cyclopropyl-α-[3-(trifluoromethyl)phenyl]-1-piperidinepropanol hydrochloride;
α-phenyl-α-tricyclo[3.3.1.13,7]dec-1-yl-1-piperidinebutanol;
α-phenyl-α-tricyclo[2.2.1.02,6]hept-3-yl-1-piperidinepropyl hydrochloride;
α-(4-amino-3,5-dibromophenyl)-α-cyclohexyl-1-piperidinebutanol;
α-(p-chlorophenyl)-α-cyclohexyl-1-piperidinepropanol hydrochloride
α-(4-amino-3-chlorophenyl)-α-cyclohexylhexahydro-1H-azepine-1-butanol;
α-cyclohexyl-α-(p-methoxyphenyl)-1-piperidinepropanol;
α-(4-amino-3,5-dichlorophenyl)-α-cyclohexylhexahydra-1H-azepine-1butanol;
α-(4-amino-3,5-dibromophenyl)-α-cyclohexyl-1,8,8-trimethyl-3-azabicyclo[3.2.1]octane-3-butanol;
α-[1,1'-biphenyl]-4-yl-α-cyclohexyl-1-piperidinepropanol hydrochloride;
α-phenyl-α-tricyclo[3.3.1.13,7]dec-1-yl-1-pyrrolidinepropanol hydrochloride;
α-phenyl-α-tricyclo[2.2.1.02,6]hept 3-yl-1-piperidinepropanol hydrochloride;
α-(3,3-dimethylbicyclo[2.2.1]hept-2-yl)-α-phenyl-1-piperdinepropanol;
α-cyclohexyl-4-hydroxy-α-4-diphenyl-1-piperidinepropanol;
α-cyclopropyl-α-[3-(trifluoromethyl)phenyl]-1-piperidinepropanol; and
α-cyclohexyl-α-phenyl-3-azabicyclo[3.2.2]nonane-3-propanol hydrochloride.

7. The method of claim 6 wherein said compound is selected from

α-cyclohexyl-α-phenyl-1-pyrrolidinepropanol hydrochloride;
α-cyclohexyl-α-phenyl-1-piperidinepropanol;
α-cyclohexyl-α-phenyl-1-piperidinepropanol hydrochloride;

α-bicyclo[2.2.1]hept-5-en-2-yl-α-phenyl-1-piperidine-propanol;

α-bicyclo[2.2.1]hept-5-en-2-yl-α-phenyl-1-piperidine-propanol hydrochloride;

3,3,5-trimethyl-α-phenyl-α-[2-(1-piperidinyl)ethylcyclohexanemethanol;

4-hydroxy-α-4-diphenyl-α-tricyclo[2.2.1.0²,⁶]hept-1-yl-1-piperidinepropanol;

α-cyclopropyl-α-[3-(trifluoromethyl)phenyl]-1-piperidinepropanol hydrochloride;

α-phenyl-α-tricyclo[3.3.1.13,7]dec-1-yl-1-piperidinebutanol;

α-phenyl-α-tricyclo[2.2.1.0²,⁶]hept-3-yl-1-piperidinepropanol hydrochloride;

α-(4-amino-3,5-dibromophenyl)-α-cyclohexyl-1-piperidinebutanol;

α-(p-chlorophenyl)-α-cyclohexyl-1-piperidine-propanol hydrochloride

α-(4-amino-3-chlorophenyl)-α-cyclohexylhexahydro-1H-azepine-1-butanol;

α-cyclohexyl-α-(p-methoxyphenyl)-1-piperidinepropanol;

α-(4-amino-3,5-dichlorophenyl)-α-cyclohexylhexahydro-1H-azepine-1-butanol;

α-(4-amino-3,5-dibromophenyl)-α-cyclohexyl-1,8,8-trimethyl-3-azabicyclo[3.2.1]octane-3-butanol;

α-[1,1′-biphenyl]-4-yl-α-cyclohexyl-1-piperidinepropanol hydrochloride;

α-phenyl-α-tricyclo[3.3.1.13,7]dec-1-yl-1-pyrrolidinepropanol hydrochloride;

α-phenyl-α-tricyclo2.2.1.0²,⁶]hept-3-yl-1-piperidinepropanol hydrochloride;

α-(3,3-dimethylbicyclo[2.2.1]hept-2-yl)-α-phenyl-1-piperidinepropanol;

α-cyclohexyl-4-hydroxy-α-4-diphenyl-1-piperidinepropanol;

α-cyclopropyl-α-[3-(trifluoromethyl)phenyl]-1-piperidinepropanol;

α-cyclohexyl-α-phenyl-3-azabicyclo[3.2.2]nonane-3-propanol hydrochloride.

8. The method of claim 7 wherein said compound is selected from procyclidine, trihexyphenidyl, biperiden and their hydrochloride salts.

9. The method of claim 7 wherein said compound is procyclidine or procyclidine hydrochloride.

* * * * *